US00PP32158P2

(12) United States Plant Patent
Hansen

(10) Patent No.: US PP32,158 P2
(45) Date of Patent: Sep. 1, 2020

(54) ***SEDUM* PLANT NAMED 'YELLOW BRICK ROAD'**

(50) Latin Name: ***Sedum kamtschaticum* (Fisch.)**
Varietal Denomination: Yellow Brick Road

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,731

(22) Filed: Nov. 26, 2019

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
CPC ... A01H 5/02; A01H 5/12; A01H 5/00; A01H 6/32; A01H 6/328
See application file for complete search history.

*Primary Examiner* — June Hwu

(57) ABSTRACT

A new and distinct cultivar of perennial *Sedum* plant named 'Yellow Brick Road' is characterized by drought-tolerant, winter-hardy, short, compact, spreading, mounded habit of stems developing reddish-purple coloration, dark-green fleshy foliage and numerous bright-yellow flowers that completely cover the plant beginning in mid-July for at least six weeks.

1 Drawing Sheet

Botanical designation: *Sedum kamtschaticum* (Fisch.).
Cultivar denomination: 'Yellow Brick Road'.

STATEMENT REGARDING PRIOR DISCLOSURES UNDER 37 CFR 1.77(B)(6)

The first public disclosure of the claimed plant, was the non-enabling photograph and brief description on a website operated by Walters Gardens, Inc. on Dec. 1, 2018. Subsequently, the claimed plant was first sold privately to Pride's Corner Farms on Apr. 15, 2019 by Walters Gardens, Inc. and then listed in the "Walters Gardens 19-20 Catalog" on May 29, 2019. Walters Gardens, Inc. obtained the new plant and all information relating thereto, from the inventor. No plants of *Sedum* 'Yellow Brick Road' have been sold under any name in this country or anywhere in the world, nor has any disclosure of the new plant been made more than one year prior to the filing date of this application, and such sale or disclosure within one year was either derived directly or indirectly from the inventor.

BACKGROUND OF THE INVENTION

The present invention relates to a new and distinct cultivar of *Sedum* or stonecrop plant, botanically known as *Sedum* and hereinafter referred to by the cultivar name 'Yellow Brick Road'.

The new plant is a hybrid selection of a planned breeding program conducted by the inventor at a wholesale perennial nursery in Zeeland, Mich., USA of a self-pollination of the proprietary, unnamed, hybrid, selection 12-67-01 (not patented). The seeds were collected in the fall of 2013, and the individual plant originating from the single seedling selection was given the breeder code 13-80-2 in 2015 at the end of the first evaluation at the same nursery.

Asexual reproduction of *Sedum* 'Yellow Brick Road' by vegetative stem cuttings and division at a wholesale perennial nursery in Zeeland, Mich., USA since the fall of 2016, has shown that the unique features of this new *Sedum* plant are stable and reproduced true to type in successive generations.

SUMMARY OF THE INVENTION

Plants of *Sedum* 'Yellow Brick Road' have not been observed under all possible environmental conditions. The phenotype may vary somewhat with variations in environment such as temperature, available water, fertility and light intensity without, however, any variation in genotype.

The following traits have been repeatedly observed and are determined to be the unique characteristics of *Sedum* 'Yellow Brick Road'. The following characteristics in combination distinguish 'Yellow Brick Road' as a new and distinct *Sedum* plant unique from all other Stonecrop plants known to the inventor:

1. Short and compact-spreading plant habit;
2. Small, dark-green, glossy foliage produced on short stiff stems;
3. Stems develop a reddish-purple blush in high light;
4. Numerous, bright yellow flowers in clusters nearly completely cover the plant for at least six weeks starting in mid-July about two weeks later than typical *Sedum kamtschaticum;*
5. Plants are drought tolerant and winter hardy from at least USDA zone 3 to 9.

The nearest comparison cultivar to the new plant known to the inventor is 'Little Miss Sunshine' U.S. Plant Pat. No. 30,039. Other similar plants include *Sedum* 'Nonel' U.S. Plant Pat. No. 23,311 and 'Nonof' U.S. Plant Pat. No. 23,313, 'Nonag' U.S. Plant Pat. No. 23,414 and 'Lime Zinger' U.S. Plant Pat. No. 24,632. 'Little Miss Sunshine' flowers earlier than the new plant with tighter cymes and less complete coverage of whole plant. 'Nonel' flowers earlier with lighter yellow flowers and shorter more drooping habit. 'Nonof' has a habit that is shorter and more sprawling, the stems are green and the flowers are earlier in the season. 'Nonag' has a more drooping habit with green stems, flowers earlier in the season and foliage that turns mahogany-colored in the winter. 'Lime Zinger' has similar habit, but the foliage is rounded and grayed-green and the flowers are cream with purplish-red tinting. The female parent was shorter in habit with more open cymes and less coverage of the flowers and without red stems. The cymes of *S. middendorfianum* are tighter with fewer flowers and less coverage of the whole plant.

BRIEF DESCRIPTION OF THE PHOTOGRAPH

The photograph of the new plant demonstrates the unique traits and the overall appearance of *Sedum* 'Yellow Brick Road'. The colors are as accurate as reasonably possible with color reproductions of this type. Variations in ambient light spectrum, source and direction may cause the appearance of minor variation in color. The plants used in the photographs were three-year-old plants grown in an open, full-sun trial garden at a wholesale perennial nursery in Zeeland, Mich. with supplemental water and fertilizer when needed. No plant growth regulators have been used.

DETAILED BOTANICAL DESCRIPTION

Figure 1:
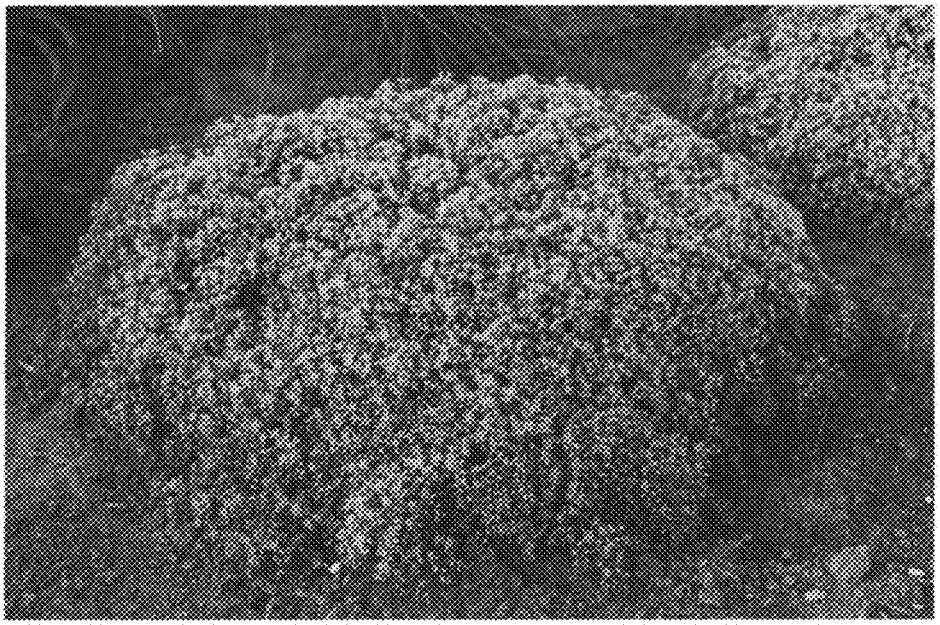
FIG. 1 shows the habit of the new plant in full flower.
Figure 2:
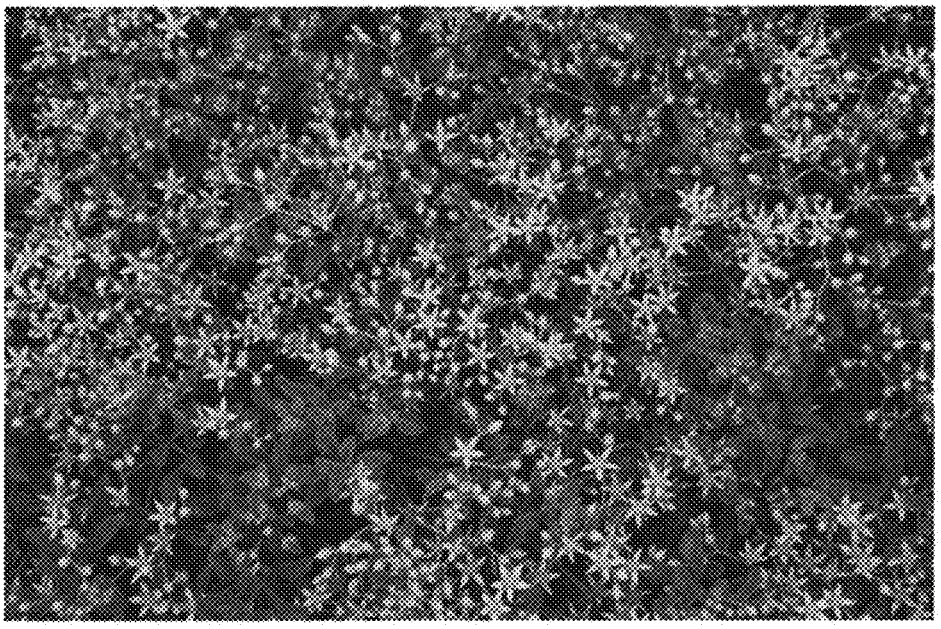
FIG. 2 shows a close-up of the foliage, stems, flowers and young flower buds.

The following is a detailed description of three-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Parentage: Self-pollination of hybrid 12-67-01 which has a proprietary selection of *Sedum kamtshaticum* (not patented);

Asexual propagation: Stem cuttings and division;

Time to initiate roots: About two weeks;

Time to finish a 3.7 liter flowering container: About 8 to 10 weeks in the summer from a rooted 2.5 cm plug;

Root description: Thick, fleshy; freely branching; creamy white to light tan in color.

Plant habit: Winter-hardy, succulent, herbaceous perennial; low mounded; multiple stiff stems, upright to outright, arising from a dense base; flower heads freely branching; dense and full, not developing open center later in the season;

Growth rate: Moderately vigorous;

Plant size: About 12.0 cm tall and 72.0 cm wide in full flower; foliage to about 10.5 cm tall and 65.0 cm wide;

Main stems: Cylindrical; glabrous; glaucous; about 112 per plant; diameter at base about 2.0 mm, about 14 cm long from base to initial flower cymes; maintaining foliage to base of stem; internodes average about 5.0 mm;

Main stem color: Variable; young regions of nearest RHS 53A. RHS 146D and RHS 146C; mature regions of nearest RHS N200A, RHS 183B, RHS 146B and RHS 146C;

Lateral branches: Typically three to five per main stem; cylindrical; glaucous; glabrous; about 1.0 mm diameter for lowest level branching and about 8.5 cm long;

Lateral branch color: Nearest RHS 183B;

Foliage: Opposite, simple; obdeltoid; sarcous; glabrous and asperous abaxial and adaxial; lustrous adaxial, and matte abaxial; base sessile and attenuate; apex rounded; margin crenate to dentate with eight teeth in distal one-third of leaf;

Leaf size: About 1.2 mm thick, fleshy and succulent; to about 22.0 mm long and about 11.0 mm across near apex and 1.0 mm wide at base; average about 19.0 mm long, about 9.0 mm across at widest portion near apex, base tapering to about 1.0 mm across; decreasing in size distally; teeth to 2 mm long and 2 mm wide at base;

Foliage color: Young developing leaves — adaxial between RHS N138B and RHS 137B, abaxial between RHS N138C and RHS 137C; fully developed leaves — adaxial between RHS 137A and RHS 137B with strong marginal blush of nearest RHS N186C, abaxial between RHS 138A and RHS 147C with light blush of nearest RHS N186C; developing in early autumn to nearest RHS 187B and RHS 187A adaxial and nearest RHS 187C abaxial;

Venation: Pinnate; color same as surrounding leaf tissue on both surfaces;

Flower: Rotate, explanate; upright; perfect; actinomophic; in terminal compound cymes; freely flowering habit with up to 60 flower buds and flowers per terminal branched cyme, 150 per branched stem and 2,000 to 5,000 per plant, covering nearly the entire foliage in peak season;

Flower size: About 14.0 mm across and 7.0 mm long;

Flower facing: Upward to outwardly;

Flower fragrance: Not detected;

Flowering season: Beginning mid-July and continuing for at least six weeks in Zeeland, Mich.;

Longevity: Individual flower remain effective for about four to six days on the plant; individual flowers persistent;

Flower buds about one day prior to opening: Ovate; apex acute; base rounded; to about 8.0 mm long and to 8.0 mm across;

Flower bud color: Exposed petals nearest RHS 7C, midrib nearest RHS 151A and sepals nearest RHS 144A;

Inflorescence: Cyme; to about 8.0 cm tall from first branch and 8.0 cm across; about 25 flowers per center cyme and 15 per cyme branch;

Petals: Typically five, lanceolate; narrowly acute apex, base truncate and fused, margin entire, glabrous; lustrous both adaxial and abaxial; typically about 6.0 mm long and about 1.5 mm across;

Petal color: Adaxial and abaxial nearest RHS 12A;

Sepals: Typically five, lanceolate; margin entire; glabrous and lustrous abaxial and adaxial; acute apex, truncate fused base; campanulate; about 3.0 mm long and about 1.0 mm wide at fused base;

Sepal color: Adaxial and abaxial nearest RHS 143A distally and proximally both adaxial and abaxial surfaces between RHS 145C and RHS N144D;

Peduncles: Glabrous; cylindrical; strong and stiff, yet flexible; freely branching; angle erect in center to nearly 60 degrees from perpendicular for branched portions; flowering portion about 8.0 cm long and 8.0 cm across;

Peduncle color: Variable; nearest RHS N200A, RHS 183B, RHS 146B and RHS 146C;

Pedicels: Short to absent; when present — cylindrical; lustrous; glabrous; strong and stiff, yet flexible; to about 3.0 mm long and 0.5 mm diameter;

Pedicel color: Variable, between RHS 183C to RHS 146C;

Androecium: Typically ten;

*Filaments*.—Thin; cylindrical; upright; fused to petal base; about 5.0 mm long and about 0.5 mm diameter; color nearest RHS 13B.

*Anthers*.—Ellipsoidal; basifixed; longitudinal; about 1.0 mm long and about 0.5 mm wide; color nearest RHS 12A.

*Pollen*.—Abundant; color nearest RHS 13A.

Gynoecium: Typically five; narrowly conical in distal one-third;

*Style*.—Narrow conical; narrowly lustrous about 4.0 mm long and 1.5 mm diameter at point of attachment to ovary; glabrous; color nearest RHS 1B.

*Stigma*.—Minute; less than 0.3 mm diameter; color nearest 12A.

*Ovary*.—Nearly cylindrical, tapering at apex to style; about 4.5 mm long and 1.5 mm diameter; color nearest RHS 144C.

Seed and fruit: Have not yet been observed, but sterility is not known;

Disease and pest resistance: Plants of the new *Sedum* 'Yellow Brick Road' grow best with good drainage, full sun and moderate to low fertility. 'Yellow Brick Road' is cold hardy from USDA zones 3 to 9. 'Yellow Brick Road' tolerates heavy rains and wind and does not tend to develop an open center later in the season as many other stonecrop cultivars do. Other pest and disease resistance and tolerance outside that normal for stonecrop is not known.

It is claimed:

1. A new and distinct perennial *Sedum* plant named 'Yellow Brick Road' as herein described and illustrated useful for landscaping as a specimen plant, en masse or as a cut flower.

* * * * *